(12) United States Patent
Leconte et al.

(10) Patent No.: US 7,687,655 B2
(45) Date of Patent: Mar. 30, 2010

(54) METHOD FOR THE PRODUCTION OF DINITRILE COMPOUNDS

(75) Inventors: Philippe Leconte, Meyzieu (FR); Beatrice Barateau, Saint Genis Laval (FR)

(73) Assignee: Rhodia Chimie, Aubervilliers (FR)

( * ) Notice: Subject to any disclaimer, the term of this patent is extended or adjusted under 35 U.S.C. 154(b) by 243 days.

(21) Appl. No.: 11/792,374

(22) PCT Filed: Nov. 30, 2005

(86) PCT No.: PCT/FR2005/002978

§ 371 (c)(1),
(2), (4) Date: Mar. 31, 2008

(87) PCT Pub. No.: WO2006/061486

PCT Pub. Date: Jun. 15, 2006

(65) Prior Publication Data

US 2009/0099386 A1    Apr. 16, 2009

(30) Foreign Application Priority Data

Dec. 7, 2004   (FR) .................................. 04 12975

(51) Int. Cl.
*C07C 253/10*   (2006.01)
*C07C 255/04*   (2006.01)
(52) U.S. Cl. ..................................... 558/338
(58) Field of Classification Search ................. 558/338

See application file for complete search history.

(56) References Cited

U.S. PATENT DOCUMENTS

| 4,434,316 | A  | 2/1984 | Barnette |
| 6,197,992 | B1 | 3/2001 | Fischer et al. |
| 2004/0122251 | A1 | 6/2004 | Rosier et al. |

FOREIGN PATENT DOCUMENTS

DE   100 46 025 A1   3/2002

OTHER PUBLICATIONS

International Search Report corresponding to PCT/FR2005/002978, issued on Feb. 17, 2006, 4 pages.

*Primary Examiner*—Kamal A Saeed
(74) *Attorney, Agent, or Firm*—Buchanan, Ingersoll & Rooney P.C.

(57) ABSTRACT

The present invention relates to a process for the manufacture of dinitrile compounds by double hydrocyanation of an olefin.

Figure 1:
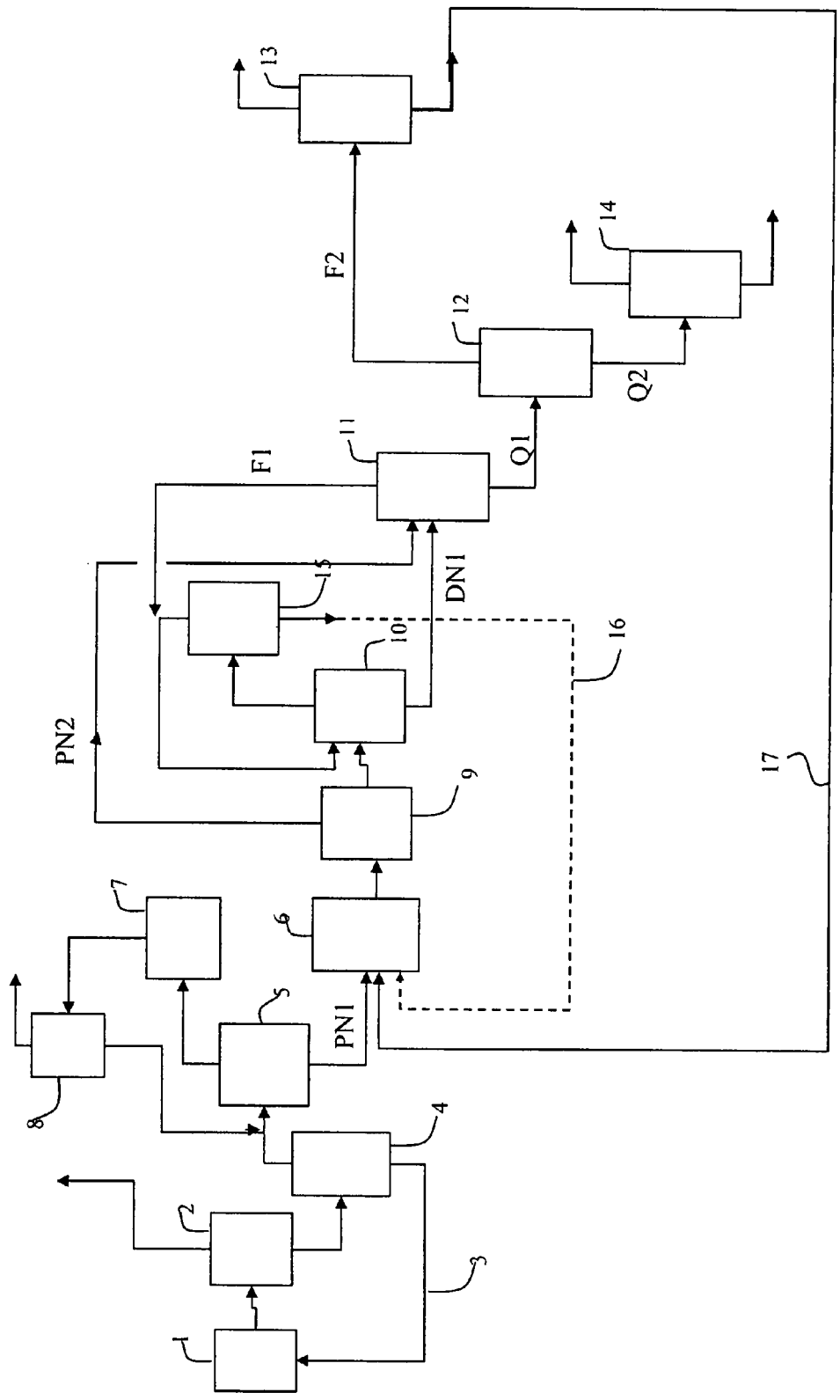

It relates particularly to a process for the manufacture of dinitrile compounds by double hydrocyanation of an olefin present in a mixture of hydrocarbons, such as a petroleum fraction and more particularly still a petroleum fraction known under the name of C4 fraction.

The process of the invention comprises a sequence of stages for the separation of the various compounds which makes it possible to remove the byproducts, such as the products from the trimerization of alkynes, present in the C4 fraction and thus to prevent their accumulation in the hydrocyanation reactors.

6 Claims, 1 Drawing Sheet

METHOD FOR THE PRODUCTION OF DINITRILE COMPOUNDS

CROSS REFERENCE TO PRIORITY APPLICATIONS

This application is the United States national phase of International Application No. PCT/FR 2005/002978, filed Nov. 30, 2005, published in French as International Publication No. WO 2006/061486 A1 on Jun. 15, 2006, and claims priority of French Application No. 0412975, filed Dec. 7, 2004, each hereby expressly incorporated by reference in its entirety and each assigned to the assignee hereof.

The present invention relates to a process for the manufacture of dinitrile compounds by double hydrocyanation of an olefin.

It relates particularly to a process for the manufacture of dinitrile compounds by double hydrocyanation of an olefin present in a mixture of hydrocarbons, such as a petroleum fraction and more particularly still a petroleum fraction known under the name of C4 fraction.

A process for the manufacture of dinitriles, in particular of adiponitrile, by double hydrocyanation of a diolefin, such as 1,3-butadiene, is known and used industrially. However, to prevent the formation of byproducts and the need to provide numerous separation stages, the 1,3-butadiene used must comprise very little in the way of impurities.

This butadiene is extracted from a petroleum fraction, referred to as C4 fraction, by an extractive distillation process.

In order to avoid these stages of separation and purification of butadiene, the proposal has been made to directly use the C4 fraction and thus a mixture of hydrocarbons comprising diolefins, such as butadiene, alkenes, in particular butenes, and alkynes.

Thus, according to U.S. Pat. No 6,197,992, the use of such a mixture of hydrocarbons is possible after having converted, in the mixture, the alkynes and the 1,2-dienes or allenes by a selective hydrogenation carried out on the mixture of hydrocarbons.

In addition, U.S. Pat. No. 4,434,316 discloses a process for the hydrocyanation of a mixture of hydrocarbons comprising diolefins and alkenes. The process makes it possible to separate and recover the alkenes, which react more slowly with hydrocyanic acid. However, this document does not disclose the process for the recovery of the products comprising a nitrile functional group.

Finally, numerous patents disclose various processes for the treatment and purification of the C4 fraction, in particular selective hydrogenation processes for converting the alkynes or the allenes into alkanes or alkenes which are not troublesome in the hydrocyanation process, at least from a chemical viewpoint.

One of the aims of the present invention is to provide a process for the manufacture of dinitrile compounds by double hydrocyanation of a mixture of hydrocarbons without preliminary treatment, in particular a mixture of hydrocarbons comprising diolefins and compounds such as alkynes.

To this end, the invention provides a process for the manufacture of dinitrile compounds by double hydrocyanation of a mixture of hydrocarbons comprising at least one diolefin and alkynes, characterized in that it consists:

in carrying out a first hydrocyanation of the diolefins by reaction between the mixture of hydrocarbons and hydrocyanic acid in the presence of a catalytic system comprising a metal in the zero oxidation state and an organophosphorus ligand, in separating the linear unsaturated nitriles from the reaction medium in order to form a first stream PN1, in carrying out, on this first stream PN1, a second hydrocyanation in the presence of hydrocyanic acid and a catalytic system comprising a metal in the zero oxidation state, an organophosphorus ligand and a Lewis acid, in at least partially separating, by distillation, the unconverted unsaturated nitrites in order to form a second stream PN2, in separating the dinitrile compounds formed from the catalytic system by a liquid/liquid extraction with a solvent in order to form a first stream of dinitriles DN1, in jointly feeding the said streams PN2 and DN1 to a distillation stage in order to produce a top fraction F1 comprising the said solvent and a bottom fraction Q1 comprising the dinitrile and unsaturated nitrile compounds, in feeding the bottom fraction Q1 to a second distillation stage in order to separate the unsaturated nitrites, forming a top fraction F2, from the dinitriles, forming a bottom fraction Q2, in feeding the bottom fraction Q2 to a third distillation stage in order to obtain a fraction comprising the linear dinitriles and a top fraction comprising the compounds with lower boiling points than that of the linear dinitriles.

The term "mixture of hydrocarbons" is understood to mean mixtures comprising at least one diolefin which makes it possible to obtain the dinitrile envisaged and other hydrocarbons, such as alkynes, alkenes, allenes or others.

Generally, these mixtures of hydrocarbons are obtained in the form of fractions, referred to as petroleum fractions, during oil refining operations.

In the preferred embodiment of the invention, that is to say the preparation of adiponitrile, the preferred petroleum fraction is the fraction referred to as the C4 fraction as it comprises in particular hydrocarbons comprising 4 carbon atoms, including the 1,3-butadiene precursor of the adiponitrile.

The process for the double hydrocyanation of a diolefin consists, in a first stage, in adding a cyano group to give a mixture of linear or branched unsaturated mononitriles, such as pentenenitriles or methylbutenenitriles in the case of the hydrocyanation of butadiene.

Among pentenenitriles, 3- and 4-pentenenitriles are the compounds which will result in adiponitrile in a second hydrocyanation stage with addition of a second cyano group to the unsaturation of the mononitriles.

These hydrocyanation reactions are carried out in the presence of homogeneous or heterogeneous catalytic systems.

Generally, the catalytic systems used are based on metal complexes of nickel in the zero oxidation state or of palladium with organophosphorus ligands, such as organophosphites, organophosphinites, organophosphonites or organophosphines, these being mono- or polydentate.

Such ligands and catalytic systems are disclosed in numerous patents, such as, for example, French Patents 1 544 656, 1 544 658, 1 589 943, 1 590 300, 1 593 627, 1 599 627 and 2 196 326. The process comprises, in addition to the two hydrocyanation stages, an isomerization stage carried out in the presence of the catalytic system described above but in the absence of hydrocyanic acid, as disclosed in French Patent 1 589 943, for example. In this stage, methylbutenenitrile is isomerized to give 3- or 4-pentenenitrile.

The second hydrocyanation stage is generally carried out in the presence of a promoter, such as a Lewis acid. Zinc chloride is the Lewis acid preferably used, in the same way as triphenylborane.

Numerous stages for the separation and purification of the various products are employed in the process for the manufacture of the dinitrile compounds by hydrocyanation of a diolefin.

Thus, at the outlet of the first reactor, the unreacted diolefin and the hydrocarbons are separated by distillation or flashing.

The nitrile compounds are subsequently separated from the catalytic system by distillation or flashing, the catalyst being recycled to the reactor.

Advantageously, the process comprises a separation by distillation of the linear unsaturated nitriles and of the branched unsaturated nitriles. The latter are introduced into an isomerization stage.

The linear unsaturated nitriles (PN1 stream) are introduced into a second hydrocyanation reactor. At the outlet of this second reactor, the unreacted nitriles are separated, at least partially, by distillation or flashing to form a stream of unsaturated nitriles PN2.

After this separation, the dinitrile compounds are separated from the catalytic system in a liquid/liquid extraction stage with a solvent of cyclohexane type, as disclosed, for example, in French Patent 2 113 471. The stream comprising the dinitriles, referred to as DN1, is introduced into various purification stages in order to extract the solvent residues, the unsaturated nitrites and, finally, the nonlinear dinitriles and various byproducts.

The stream of nitriles PN2 is, according to the invention, mixed with the stream DN1 at one of these purification stages, preferably before the stage of separation of the unsaturated nitrile compounds and more preferably still before the column for separation of the solvent used in the liquid/liquid extraction, as indicated below.

According to one characteristic of the invention, the purification of the stream of dinitriles DN1 is carried out, in the first place, in a column which makes it possible to separate the solvent from the nitrile compounds, the stream PN2 of mononitriles being fed in conjunction with the stream DN1 to this stage of separation of the solvent.

The bottom fraction Q1 comprising the dinitrile and unsaturated nitrile compounds is then fed to a second distillation stage in order to separate the dinitriles from the unsaturated mononitriles. The latter, present in the top fraction F2, are advantageously recycled, after separation of the conjugated unsaturated mononitriles, to the second hydrocyanation reactor.

In one embodiment of the invention, the separation of the solvent and of the unsaturated mononitriles can be carried out in a single column, instead of the two columns as described above.

Finally, the linear dinitriles, such as adiponitrile, forming the bottom fraction Q2 are recovered in a distillation stage in order to separate the linear dinitriles from the branched dinitriles, such as methylglutaronitrile.

The process of the invention makes it possible to use, as source of diolefins, a mixture of hydrocarbons comprising in particular alkyne compounds. This is because these compounds, brought into the presence of the hydrocyanation catalytic system, can trimerize. Thus, in the case of a C4 fraction which comprises propyne or butyne, the latter, by trimerization, will produce trimethylbenzene (TMB) and triethylbenzene (TEB). These compounds have boiling points which are between those of the unsaturated nitrites and the dinitriles.

According to the process of the invention, as the mononitriles of the PN2 stream are mixed with the DN1 stream, it is possible to recover, for the purpose of recycling them in the hydrocyanation process, the pentenenitriles devoid of byproducts of TMB and/or TEB type as the latter will remain in the fraction comprising the dinitriles. This is because, in the column for separation between the dinitriles and the mononitriles, the trimerization products will be found in the bottom fraction, that is to say in the fraction comprising the dinitriles. Thus, the unsaturated mononitriles which are recycled to the second hydrocyanation reactor will no longer comprise trimerization products. The latter will be bled off and separated from the dinitrile compounds in one of the stages for the purification of the dinitriles.

The process of the invention thus makes it possible to remove the trimerization products while preventing their accumulation in and recycling to the second hydrocyanation reactor.

The process of the invention thus makes it possible to use, as starting material, a mixture of hydrocarbons comprising at least one diolefin and other compounds, such as alkynes.

In the case of the manufacture of adiponitrile, an important chemical intermediate in the manufacture of monomers of polyamides, such as hexamethylenediamine or caprolactam, the process of the invention makes it possible to use unpurified butadiene, in particular comprising alkynes. This result is important from an economic viewpoint as the separation of the alkynes and of the butadiene requires distillation stages which are difficult and expensive in capital costs.

The process of the invention can comprise other stages which make it possible in particular to separate the catalyst or to extract the catalyst residues present in the solid form, such as the metal element in the oxidized state.

The process of the invention thus makes it possible to use, as starting materials for the manufacture of adiponitrile, mixtures of hydrocarbons comprising butadiene and in particular the C4 petroleum fraction produced industrially. This C4 fraction can be used directly without preliminary treatment or after partial purification. However, it is not necessary to carry out a purification in order to extract the alkyne compounds from this fraction.

Other advantages and details of the invention will become clearly apparent in the light of an embodiment of the process of the invention produced with reference to the single appended FIGURE in which a block diagram of the process of the invention is represented.

According to one embodiment of the invention, a mixture of hydrocarbons forming a C4 petroleum fraction is fed to a hydrocyanation reactor 1 with hydrocyanic acid. The reactor is a conventional reactor for carrying out a reaction under pressure at high temperature. The catalytic system used is, in the example of the invention, a complex of nickel in the zero oxidation state with triphenyl phosphite.

The conditions of this reaction are disclosed in the literature, for example in the abovementioned patents and Patents EP 1 344 770 and U.S. Pat. No. 5,981,772.

The reaction medium is withdrawn from the reactor 1 and the unconverted hydrocarbons are separated in a column 2.

The stream comprising the unsaturated nitrile compounds is fed to a flashing column 4 which makes it possible to separate, at the bottom, the catalytic system, which is recycled to the reactor 1 via the pipe 3, and, at the top, the organic compounds, in particular the unsaturated nitrile compounds.

The stream comprising the mononitrile compounds is advantageously fed to a distillation column 5 in order to recover, as top fraction, the branched unsaturated nitrites, such as 2-methyl-3-butene-nitrile (2M3BN), and, as bottom fraction, the linear unsaturated nitrile compounds, such as 3-pentenenitrile or 4-pentenenitrile, forming the stream PN1.

The latter stream is fed to the second hydrocyanation reactor 6.

The stream comprising the branched nitriles is fed to an isomerization reactor 7. This isomerization reaction is carried out according to the conditions disclosed, for example, in U.S. Pat. No. 5,981,772 and FR 1 589 943.

The catalytic system used in this isomerization stage is advantageously identical to that used in the reactor 1 for the first hydrocyanation stage.

The reaction medium resulting from the isomerization reactor 7 is flashed in order to separate the nitrile organic compounds from the catalyst. The nitrile compounds recovered are fed to a distillation stage 8 in order to separate, at the top, the branched conjugated nitrile compounds from the unconjugated nitrile compounds as bottom fraction. This bottom fraction is conveyed to the feed of the column 5 for separation of the linear nitriles and branched nitriles.

At the outlet of the second hydrocyanation reactor 6, the reaction medium is subjected to a distillation stage 9 or flashing in order to separate the unconverted mononitriles, collected as top fraction and forming the stream PN2.

The bottom fraction comprising the dinitriles and the catalytic system is fed to various separation stages, including a liquid/liquid extraction 10, in order to separate the dinitriles from the catalytic system and to recover the latter after separation from the solvent 15 for recycling via the pipe 16.

The liquid/liquid extraction is carried out in the presence of a hydrocarbon solvent which makes it possible to extract the organometallic complex. Mention may be made, as suitable hydrocarbon solvent, of cyclohexane.

The phase comprising the dinitriles and a small amount of solvent, forming the stream DN1, is, according to the invention, mixed with the stream PN2 of mononitriles recovered at the outlet of the separation stage 9.

This mixture is fed to a distillation column 11 in order to separate, as top fraction F1, the residual solvents, such as the cyclohexane.

The bottom fraction Q1 is fed to a further distillation column 12 in order to recover, as top fraction F2, the mononitriles and, as bottom fraction Q2, the dinitriles.

According to the invention, the compounds from the trimerization of the alkynes, such as TMB or TEB, are also recovered in the bottom fraction Q2 comprising the dinitriles.

Thus, the top fraction F2 comprising the mononitriles can be recycled to the second hydrocyanation reactor 6 via the pipe 17 after having been subjected to a purification in 13 in order to remove the mononitriles which cannot be enhanced in value to give adiponitrile, such as 2-pentenenitrile or valeronitrile.

The stream Q2 comprising the dinitriles is subsequently fed to a purification stage 14 which can comprise several distillation columns arranged in series which makes it possible to recover a fraction comprising the branched dinitriles, such as 3-methylglutaronitrile, and the products resulting from the trimerization of the alkynes (TMB, TEB) and a fraction comprising the linear dinitriles, such as adiponitrile.

The process of the invention thus makes it possible to remove, as effluents, the products from the trimerization of the alkynes introduced with the mixture of hydrocarbons or any other product with a boiling point between those of the nitriles and the dinitriles.

A test was carried out in which a mixture comprising adiponitrile, methylglutaronitrile, 3-pentenenitrile, cyclohexane and trimethylbenzene (TMB) is fed to the distillation column 11. The concentration by weight of the TMB is 0.1%. This mixture is fed according to a flow rate of 640 g/h.

The top fraction of the column 11 is composed of cyclohexane and does not comprise TMB.

The bottom fraction comprising the TMB is fed to the column 12 for separation of the mononitriles, in particular 3-pentenenitrile.

The top fraction recovered in the column 12 is composed mainly of 3-PN. The concentration by weight of TMB is 0.0005%.

The bottom fraction, comprising the dinitriles, is fed to the column 14 for separation and purification of the linear dinitriles. The top fraction, comprising in particular the branched dinitriles, also comprises TMB. The amount of TMB recovered in this top fraction represents substantially all of the TMB introduced into the column 11 (99.9% of the amount introduced).

Of course, the process of the invention can comprise other stages for separation and purification of the various streams without, on that account, departing from the scope of the invention.

The invention claimed is:

1. A process for the production of dinitrile compounds by double hydrocyanation of a mixture of hydrocarbons containing at least one diolefin, which comprises:
    conducting a first hydrocyanation of the diolefins by reaction between the mixture of hydrocarbons and hydrocyanic acid in the presence of a catalytic system comprising a metal in the zero oxidation state and an organophosphorus ligand,
    separating the linear unsaturated nitriles from the reaction medium to form a first stream PN1,
    conducting, on this first stream PN1, a second hydrocyanation in the presence of hydrocyanic acid and a catalytic system comprising a metal in the zero oxidation state, an organophosphorus ligand and a Lewis acid,
    separating from the reaction medium, by distillation, the unconverted unsaturated nitriles to form a second stream PN2,
    separating, in the reaction medium, the dinitrile compounds formed from the catalytic system by a liquid/liquid extraction with a solvent to form a first stream of dinitriles DN1,
    jointly feeding the said streams PN2 and DN1 to a distillation stage to produce a top fraction F1 comprising the said solvent and a bottom fraction Q1 comprising the dinitrile and unsaturated nitrile compounds,
    feeding the bottom fraction Q1 to a second distillation stage to separate the unsaturated nitriles, forming a top fraction F2, from the dinitriles, and forming a bottom fraction Q2,
    feeding the bottom fraction Q2 to a third distillation stage to obtain a fraction comprising the linear dinitriles and a top fraction comprising the compounds with lower boiling points than that of the linear dinitriles.

2. The process as defined by claim 1, said mixture of hydrocarbons comprising butadiene.

3. The process as defined by claim 1, said mixture of hydrocarbons comprising a C4 petroleum fraction.

4. The process as defined by claim 1, said catalytic system comprising a complex of nickel in the zero oxidation state with an organophosphorus compound.

5. The process as defined by claim 1, wherein the solvent employed in the liquid/liquid extraction stage comprises cyclohexane.

6. The process as defined by claim 1, wherein the Lewis acid is selected from the group consisting of zinc chloride and triphenylborane.

* * * * *